US009610329B2

(12) United States Patent
Steiner et al.

(10) Patent No.: US 9,610,329 B2
(45) Date of Patent: *Apr. 4, 2017

(54) STABILIZED GLUCAGON SOLUTIONS

(75) Inventors: Solomon S. Steiner, Mount Kisco, NY (US); Robert Hauser, Columbia, MD (US); Ming Li, Yorktown Heights, NY (US); Robert Feldstein, Yonkers, NY (US); Roderike Pohl, Sherman, CT (US)

(73) Assignee: Albireo Pharma, Inc., Boston, MA (US)

( * ) Notice: Subject to any disclaimer, the term of this patent is extended or adjusted under 35 U.S.C. 154(b) by 1224 days.

This patent is subject to a terminal disclaimer.

(21) Appl. No.: 12/891,240

(22) Filed: Sep. 27, 2010

(65) Prior Publication Data
US 2011/0237510 A1    Sep. 29, 2011

Related U.S. Application Data

(63) Continuation-in-part of application No. 12/715,203, filed on Mar. 1, 2010.

(60) Provisional application No. 61/254,128, filed on Oct. 22, 2009, provisional application No. 61/327,440, filed on Apr. 23, 2010.

(51) Int. Cl.
| A61K 38/26 | (2006.01) |
| A61K 9/107 | (2006.01) |
| A61K 47/24 | (2006.01) |
| A61K 47/26 | (2006.01) |
| A61K 9/00  | (2006.01) |
| A61K 9/19  | (2006.01) |

(52) U.S. Cl.
CPC ............ *A61K 38/26* (2013.01); *A61K 9/0019* (2013.01); *A61K 9/1075* (2013.01); *A61K 9/19* (2013.01); *A61K 47/26* (2013.01)

(58) Field of Classification Search
USPC ....................................................... 514/7.2
See application file for complete search history.

(56) References Cited

U.S. PATENT DOCUMENTS

| 5,652,216 | A | 7/1997 | Kornfelt |
| 6,384,016 | B1* | 5/2002 | Kaarsholm ............... 514/11.7 |
| 2006/0084605 | A1* | 4/2006 | Engelund et al. ........... 514/12 |
| 2006/0183682 | A1 | 8/2006 | Juul-Mortensen |
| 2006/0293382 | A1* | 12/2006 | Weldele et al. ............ 514/457 |
| 2007/0010424 | A1* | 1/2007 | Pedersen et al. ............ 514/3 |

FOREIGN PATENT DOCUMENTS

| EP | 1061947 | 12/2000 |
| GB | 1202607 | 8/1970 |
| WO | 9947160 | 9/1999 |
| WO | 0149314 | 7/2001 |

OTHER PUBLICATIONS

International Search report for PBT/US2010/050386 mailed Oct. 12, 2011.
Aboul-Fadl, "Antisense oligonucleotides: the state of the art.", Curr. Med. Chem., 12(19):2193-2214 (2005).
Bösch, et al., "Physicochemical characterization of glucagon-containing lipid micelles.", Biochim. Biophys. Acta, 603(2):298-312 (1980).
Gregoriadis, et al., "Improving the therapeutic efficacy of peptides and proteins: a role for polysialic acids.", Int. J. Pharm., 300(1-2)125-130 (2005).
Gregoriadis and Ryman, "Liposomes as carriers of enzymes or drugs: a new approach to the treatment of storage diseases.", Biochem. J., 124(5):58P (1971).
Gregoriadis, "The carrier potential of liposomes in biology and medicine (second of two parts).", N. Engl. J. Med., 295(14):765-770 (1976).
Hamed, et al., "Behavior of amphipathic helices on analysis via matrix methods, with application to glucagon, secretin, and vasoactive intestinal peptide.", Biopolymers, 22 (3):1003-1021 (1983).
Matilainen, et al., "The effect of cyclodextrins on chemical and physical stability of glucagon and characterization of glucagon/gamma-CD inclusion complexes.", J. Pharm. Sci., 97(7):2720-2729 (2008).
Matilainen, et al., "The stability and dissolution properties of solid glucagon/gamma-cyclodextrin powder.", Eur. J. Pharm. Sci., 2;36(4-5):412-420 (2009).
Robinson, et al., "Lipid-induced conformational changes in glucagon, secretin, and vasoactive intestinal peptide", Biopolymers, 21(6):1217-1228 (1982).
Sapra, et al., "Ligand-targeted liposomes for cancer treatment.", Curr. Drug Deliv., 2(4):369-381 (2005).
Schneider, et al., "Polypeptide hormone interaction, II. Glucagon binding to lysolecithin.", J.Biol. Chem., 247(16):4986-4991 (1972).
Schneider, et al., "Polypeptide Hormone Interaction: III. Conformational Changes of Glucagon Bound to Lysolecithin", J.Biol. Chem., 247(16):4992-4996 (1972).
Tyagi, et al., "Urodynamic and immunohistochemical evaluation of intravesical capsaicin delivery using thermosensitive hydrogel and liposomes.", J. Urol., 171(1):483-489 (2004).
Wu, et al., "Helical conformation of glucagon in surfactant solutions.", Biochemistry, 19(10):2117-2122 (1980).

* cited by examiner

*Primary Examiner* — Julie Ha
*Assistant Examiner* — Kristina M Hellman
(74) *Attorney, Agent, or Firm* — Pabst Patent Group LLP

(57) ABSTRACT

A formulation composed of a sugar such as glucose and a surfactant such as myristoyl lysophosphocholine (LMPC) has been designed to stabilize both hydrophilic and hydrophobic portions of the glucagon molecule, under prolonged physiological conditions, in a formulation that is sufficiently similar to the pH and osmolarity of plasma so as not to induce or to minimize site irritation. The combination of a simple sugar and an surfactant stabilizes the glucagon molecule in an aqueous solution for seven days at 37° C.

23 Claims, 5 Drawing Sheets

STABILIZED GLUCAGON SOLUTIONS

CROSS-REFERENCE TO RELATED APPLICATIONS

This application is a continuation in part of U.S. Ser. No. 12/715,203 filed on Mar. 1, 2010, and claims benefit of and priority to U.S. Provisional Patent Application No. 61/254,128 filed on Oct. 22, 2009 and U.S. Provisional Patent Application No. 61/327,440 filed on Apr. 23, 2010, each of which is incorporated herein by reference in their entirety.

FIELD OF THE INVENTION

This disclosure generally relates to stabilized glucagon solutions.

BACKGROUND OF THE INVENTION

Glucagon is synthesized in the pancreas. It is a highly conserved polypeptide consisting of a single chain of 29 amino acids, with a molecular weight of 3485 Da. Recombinant glucagon is expressed in *E. coli* and purified to at least 98% pure prior to use. Proteolytic removal of the amino-terminal histidine residue leads to loss of the biological activity. Glucagon has a helical conformation in the crystalline state, while in dilute aqueous solutions it has a random coil conformation with 15% alpha helix at the C-terminal end.

Pharmacologically, glucagon increases the concentration of glucose in the blood. The first six amino acids at the N-terminus of the glucagon molecule bind to specific receptors on liver cells. This leads to an increase in the production of cAMP, which facilitates the catabolism of stored glycogen and increases hepatic gluconeogenesis and ketogenesis. The immediate pharmacologic result is an increase in blood glucose at the expense of stored hepatic glycogen. The onset of action post injection is 5-20 minutes. Glucagon is degraded in the liver, kidney, and tissue receptor sites. The half life of glucagon in plasma is 3 to 6 minutes, similar to that of insulin.

Glucagon is soluble in aqueous solutions at pH less than 3 or greater than 9, and has low solubility in the pH range of 4 to 8 due to its isoelectric point of 7.1. It forms a gel in acidic aqueous conditions (pH 3-4) and precipitates within an hour of preparation in a neutral aqueous solution.

Currently, the commercial preparation of glucagon is a two part sterile vial, intended for immediate use following reconstitution. It is sold as a rescue kit and is available for intravenous, intramuscular or subcutaneous administration. The kit contains 1 mg (1 unit) of glucagon and 49 mg of lactose in a sterile vial. The diluent contains 12 mg/mL glycerin, water for injection and hydrochloric acid. The diluent is injected into the powder vial, gently swirled to dissolve the glucagon, then the glucagon solution is pulled back into the same syringe ready for injection. The pH of this solution is approximately 2. The recommended dose is typically 0.5-1 mg. Any reconstituted glucagon is to be discarded since it is not stable in solution.

Previous attempts to stabilize glucagon include the addition of cationic or anionic monovalent detergents to enhance the solubilization of 1 mg/mL glucagon using a 6 fold molar excess of detergent, as described in GB Patent No. 1202607; hen egg lysolecithin, which shows the detergent induced partial helical structure in solutions of glucagon containing about 0.02 mg/ml peptide, as described in J. Biol. Chem. 247, 4986-4991; 4992-4996 (1972); lysolecithin, as described in Biopolymers 21, 1217-1228 (1982), Biopolymers 22, 1003-1021 (1983); micelles of anionic detergent SDS at low pH, as described in Biochem. 19, 2117-2122 (1980), and at neutral pH, as described in Biochim. Biophys. Acta 603, 298-312 (1980); and cyclodextrins (J. Pharm Sci. 97(7):2720-9 (2008)); Eur J Pharm Sci. 2; 36 (4-5):412-20 (2009). EP 1061947 by Novo Nordisk describes stabilized glucagon solutions containing surfactant such as LPMC or other detergents carrying multiple charges (two or more negative, two or more positive, or both positive and negative) added in 0.5-20 moles detergent/peptide), solubilizing glucagon at pharmaceutically relevant concentrations in the entire pH range of 4 to 9. U.S. Pat. No. 5,652,216 to Kornfelt, et al., describes a pharmaceutical preparation comprising glucagon and a stabilizing amount of a pharmaceutically acceptable ampholyte such as an amino acid or dipeptide or a mixture thereof and optionally an excipient.

Recently, glucagon is being developed for use in an "artificial pancreas" or bihormonal pump. Insulin pumps have been used by insulin dependent diabetics for over a decade. These pumps are capable of providing a continuous flow of insulin to cater to their basal insulin needs. After eating, the user can manually increase the insulin flow to temporarily cover their meal, then cut back to the slow basal flow. These apparatus are attached to the abdominal surface by a small needle and may remain in place for up to a week. Newer devices also have been developed that combine the ability to read the patient glucose levels and deliver insulin as needed to cover individual patient requirements. However, should too much insulin be given, there is no way to prevent hypoglycemia. Therefore, the next step to complete the artificial pancreas is to add a second pump to deliver glucagon to the patient to counteract hypoglycemia. This creates an artificial pancreas capable of keeping a patient within ideal glucose levels, similar to how a normal functioning pancreas does in a non-diabetic individual. However, this application requires a glucagon that is stable in solution for at least seven days at 30-37° C., and the current commercial formulations are not capable of fulfilling that need. Moreover, since the currently available formulation is designed for "rescue" use, the acidic nature and pain of the injection is acceptable since it is a single dose, rarely given to the patient. However, the pH and isotonicity of the solution should be closer to physiological conditions for use in a pump.

It is therefore an object of the present invention to provide a glucagon that is stable as a clear solution for at least seven days at 37° C. for extended use in a pump device.

SUMMARY OF THE INVENTION

A formulation composed of a sugar such as glucose and a surfactant such as myristoyl lysophosphocholine (LMPC) has been designed to stabilize both hydrophilic and hydrophobic portions of the glucagon molecule, thereby preventing gelation for extended periods of time. To further retard gelation, a small amount of alcohol such as ethanol may be added to the formulation. A buffer such as phosphate may be added to stabilize pH. The combination of glucose, a simple sugar, and LMPC, an amphiphilic surfactant, stabilizes the glucagon molecule in an aqueous solution for at least seven days at 37° C. at physiological pH. Addition of ethanol further retards gelation of glucagon beyond 20 days at 25° C. Additional excipients may be added to stabilize the formulation, control gelation or viscosity. The formulation is preferably a clear solution, but may contain micelles, be in the form of a microemulsion, liposomes, or microsuspension. The most preferred embodiment is a clear solution that may contain micelles. In the preferred embodiment, the stabilized glucagon formulation contains water, lyso myristoyl phosphocholine (LMPC), glucose, ethanol and optionally a preservative such as sodium benzoate, benzyl alcohol or m-cresol and/or a buffer to hold the desired pH such as phosphate. The concentration range for glucagon is 0.5-5 mg/mL, preferably 0.8 to 1.5 mg/mL; glucose 20-100 mg/mL, preferably 36 to 72 mg/mL; LMPC 0.1-10 mg/mL, preferably 0.5-5 mg/mL; ethanol 0.5-10%, preferably 2-5%; preservatives sodium benzoate, benzyl alcohol, or m-cresol 0.2 to 3 mg/mL; phosphate buffer 1-30 mM, preferably 5 mM-10 mM.

In the preferred embodiment, the product may be produced and stored at 4° C. as a clear, one part solution ready for injection subcutaneously, intramusculary, or intravenously. In another embodiment, the one part formulation may be stored frozen and thawed before use. In another embodiment, the glucagon is lyophilized in the presence of glucose and surfactant, preferably LMPC, to stabilize the powder, and on reconstitution assist in stabilizing the glucagon in solution. The diluent may contain a preservative, such as sodium benzoate, benzyl alcohol or m-cresol. This system works as a two part diluent and dry powder system that is stable at room temperature. On reconstitution of the powder with the diluent, the resulting clear solution may be used up to 7 days next to the body at a temperature of 30-37° C., for example, in a bihormonal pump.

DETAILED DESCRIPTION OF THE INVENTION

I. Definitions

As used herein, "glucagon" refers to the full length peptide, glucagon. "GLP-1" refers to glucagon-like peptides (GLP-1, amino acids 7-36 amide and 7-37), and analogs and derivatives thereof, unless otherwise specified.

As used herein, BIOD 901 is 1 mg glucagon/mL, 2 mg LMPC/ml, 45 mg glucose/ml and 2 mg m-cresol/mL, approximately pH 7.3.

As used herein, BIOD 902 is 1 mg glucagon/mL, 2 mg LMPC/mL, 45 mg glucose/mL, 2 mg m-cresol/mL and 5 mM phosphate buffer, pH 7.3.

A gel is a solid or a semisolid system of at least two constituents, consisting of a condensed mass enclosing and interpenetrated by a liquid. A gel may consist of macromolecules existing as twisted, matted strands. The units are often bound together by stronger types of van der Waals forces so as to form crystalline and amorphous regions throughout the entire system. These gels are considered to be one-phase systems because no definite boundaries exist between the dispersed macromolecules and the liquid.

A gel in water, also known as hydrogel, is a disperse phase (colloid particles) combined with continuing phase (water) to form viscous jelly-like 3-dimension network. In general, two classes of hydrogel can be defined, physical gels (pseudogels) where the macromolecular chains are connected by electrostatic forces, hydrogen bonds, hydrophobic interactions or chain entanglements; and chemical gels (permanent), where the chains are linked by covalent bonds.

As used herein, gelation refers to the formation of gel particles and gel network in the solution. The gel can be destroyed by mechanical stirring, but the content of the macromolecule (glucagon) is not typically recovered. Gelation in formulations can be detected by an decrease of 5% or more of transmitted light through the solution (light obscuration) or by an increase in particle size (Malvern nanosizing).

As used herein, chemical instability refers to a loss of glucagon into breakdown products that can be quantitated by HPLC.

As used herein, physical instability refers to gelation, fibril formation or precipitation of the clear glucagon solution.

As used herein, a "sugar" refers to a monosaccharide or disaccharide, small organic molecules that contain multiple hydroxy groups and an aldehyde or ketone functional group. Saccharides can exist in both a straight chain or cyclic conformation. Preferred examples include sucrose, maltose and glucose.

As used herein, "osmolarity" is the concentration of a solution in terms of milliosmoles of solutes per liter of solution. The normal plasma osmolarity is in the range of 280-310 mOs/kg.

As used herein, "prolonged" refers to a period of five to ten days, preferably seven to ten days.

As used herein, "physiological pH" is in the range of 6.8 to 7.5, preferably 7 to 7.4.

As used herein, "physiological temperature" is between 30 and 37° C.

II. Formulations

A. Glucagon

Figure 1:
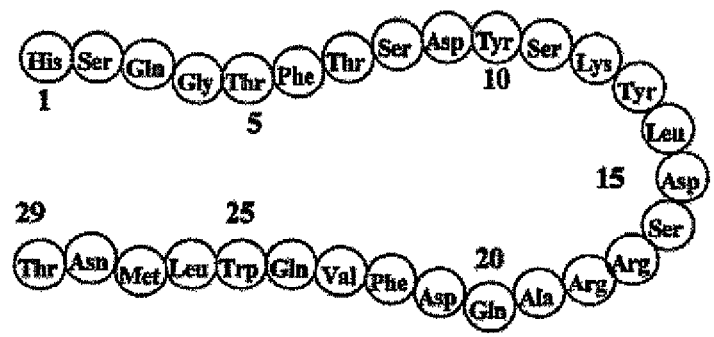
FIG. 1 is a schematic of the structure of glucagon.

Glucagon is a highly conserved polypeptide consisting of a single chain of 29 amino acids (FIG. 1), with a molecular weight of 3485 Da, synthesized in the pancreas. Recombinant glucagon is expressed in *E. coli* and purified to at least 95% pure prior to use. Natural and recombinant glucagon are bioequivalent, as demonstrated by Graf, et al., J. Pharm. Sci. 88(10):991-995 (2000). Multiple commercial sources are available. The preferred concentration range for glucagon is 0.5-5 mg/mL, preferably 0.8 to 1.5 mg/mL, most preferably 1 mg/mL.

B. Sugars

"Sugar" refers to a monosaccharide or disaccharide, small organic molecule that contains multiple hydroxy groups and an aldehyde or ketone functional group, but not polyols such as glycerol. Saccharides can exist in both a straight chain or cyclic conformation. Preferred examples include sucrose, maltose and glucose or lactose in a concentration range of about 20-100 mg/mL, preferably 0.25 M.

C. Surfactants

Amphiphilic surfactants (i.e., having at least two positive and two negative charges in different regions of the molecule) such as phospholipids or glycerophospholipids, containing a polar head and two non-polar tails, in combination with sugars are useful in stabilizing the glucagon. These are preferably GRAS ("generally regarded as safe") phospholipids or endogenous phospholipids. The surfactant may be a sn-glycero-3-phosphate ester of ethanolamine, choline, serine or threonine. Octanoyl, decanoyl, lauroyl, palmitoyl and myristoyl derivatives of lysophosphatidylcholine, lysophosphatidylserine and lysophosphatidylthreonine, are particularly useful.

In the preferred embodiment, the surfactant is LMPC. Surfactant is added in a concentration equivalent to LMPC in a range of 0.1-10 mg/mL, preferably 0.5-5 mg/mL. A preferred concentration is 2 mg surfactant/mL with glucose at 0.25 M. It is likely the LMPC forms micelles in solution.

Other surfactants may interact with the glucagon solution to form liposomes. Liposomes (LPs) are spherical vesicles, composed of concentric phospholipid bilayers separated by aqueous compartments. LPs have the characteristics of adhesion to and creating a molecular film on cellular surfaces. Liposomes are lipid vesicles composed of concentric phospholipid bilayers which enclose an aqueous interior (Gregoriadis, et al., Int J Pharm 300, 125-30 2005; Gregoriadis and Ryman, Biochem J 124, 58P (1971)). The lipid vesicles comprise either one or several aqueous compartments delineated by either one (unilamellar) or several (multilamellar) phospholipid bilayers (Sapra, et al., Curr Drug Deliv 2, 369-81 (2005)). The success of liposomes in the clinic has been attributed to the nontoxic nature of the lipids used in their formulation. Liposomes have been widely studied as drug carriers for a variety of chemotherapeutic agents (approximately 25,000 scientific articles have been published on the subject; see Gregoriadis, N Engl J Med 295, 765-70 (1976); Gregoriadis, et al., Int J Pharm 300, 125-30 (2005)). Water-soluble anticancer substances such as doxorubicin can be protected inside the aqueous compartment(s) of liposomes delimited by the phospholipid bilayer(s), whereas fat-soluble substances such as amphotericin and capsaicin can be integrated into the phospholipid bilayer (Aboul-Fadi, Curr Med Chem 12, 2193-214 (2005); Tyagi, et al., J Urol 171, 483-9 (2004)).

The formulation can also be provided as an emulsion, microemulsion (<100 nm) or micelles, formed by addition of water to the surfactant, or surfactant to the water. Liposomes and emulsions are not preferred for use with a pump or other small orifice means for administration, due to the inherently more viscous nature of liposomes and emulsions.

Non-ionic surfactants such as methyl beta cyclodextran or polysorbates (such as TWEEN® 20) also may be used to control gelation of the above excipients and/or glucagon.

D. Anti-Gelling Agents

Materials such as ethanol can be added to the glucagon formulation to inhibit gel formation during storage, especially at 4° C. Studies using 0.5 to 40% ethanol added to glucagon have shown that ethanol can be added up to 10%, most preferably at 2% v/v, to prevent gelation. Other examples of alcohols that inhibit gelation include monohydric alcohols such as pentanol (amyl alcohol) and hexadecane-1-ol (cetyl alcohol, palmityl alcohol). Polyhydric alcohols, such as propane 1,2,3,triol (glycerin), butane 1,2,3,4-tetraol (erythritol), Pentane-1,2,3,4,5,6-hexol (mannitol, sorbitol) and heptanes-1,2,3,4,5,6,7-heptol (volemitol); unsaturated aliphatic alcohols such as 3,7-dimethylocta-2,6-dien-1-ol (Geraniol); and alicyclic alcohols such as cyclohexane-1,2,3,4,5,6-geksol (inositol) and 2-(2-propyl)-5-methyl-cyclohexane-1-ol (menthol).

The prevention of gelation can be measured using any of several known assays. For example, a formulation is confirmed to be gelled if there is 5% or more obscuration of light compared to fresh sample, as demonstrated in Example 6. Alternatively the size distribution of the formulation can be evaluated by a Malvern nanosizer. If the primary particle size of the clear solution increases (approximately doubles in size distribution) compared to the initial primary particle size, the sample is gelling.

E. Optional Excipients:

Preservatives

Preservatives such as EDTA, sodium benzoate, meta-cresol, and benzyl alcohol may be added to the formulation to a concentration of 0.2 to 3 mg/mL. The preservative may be present in the liquid formulation, or in the diluent for the two part lyophilized presentation.

Osmolarity

Excipients may also be added to adjust osmolarity. For example, glycerol, in a final concentration of 1-22 mg/mL, may be used to adjust osmolarity.

Buffering Agents

Buffers such as phosphate, citrate, glycine or acetate may be used to stabilize the pH of the formulation. The concentration range is 1-30 mM, preferably 5-10 mM.

III. Methods of Reconstitution, Manufacture and Use

In the preferred embodiment, the product is a clear one part solution, stored frozen or at 4° C. ready for injection. In the preferred embodiment shown in the examples, the stabilized glucagon solution contains water, lyso myristoyl phosphocholine (LMPC), glucose, ethanol, and, optionally sodium benzoate and/or phosphate buffer. The concentration range for glucagon is 0.5-5 mg/mL, preferably 0.8 to 1.5 mg/mL; glucose 20-100 mg/mL, preferably 36 to 72 mg/mL; LMPC 0.1-10 mg/mL, preferably 0.5-5 mg/mL; ethanol 0.5-10%, preferably 2-5%; preservative sodium benzoate or benzyl alcohol 0.2 to 3 mg/mL, phosphate buffer 0.5-10 mM, preferably 5 mM. The final pH of the solution is in the range of 2-8, preferably 5-7.6. The osmolarity is in the range of 200-400 mOsm, preferably 240-310 mOsm.

In one embodiment, the glucagon is lyophilized in the presence of glucose and surfactant, preferably LMPC, to stabilize the powder, and on reconstitution assists in stabilizing the glucagon in solution. The diluent may contain a preservative, preferably sodium benzoate, benzyl alcohol or m-cresol. This system works as a two part diluent and dry powder system that is stable at room temperature. On reconstitution of the powder with the diluent, the resulting clear solution may be used up to 7 days next to the body at a temperature of 30-37° C. The final pH of the reconstituted solution is in the range of 4-8, preferably 5-7.6. Osmolarity in the range of 200-400 mOsm, preferably 240-310 mOsm.

To use the glucagon in a pump, pump cartridges are prefilled. In one embodiment, the cartridges are shipped and stored frozen and thawed prior to use in the pump. The glucagon may also be provided in a kit containing two injection vials, one containing a dry sterile powder glucagon and the other a sterile diluent. The resulting volume of both vials is from 1 to 5 mL, depending on the volume to be dispensed by the pump device. At the time of use, the contents of the diluent vial are added to the glucagon vial via a transfer syringe and gently swirled to reconstitute. Then a 1 to 3 mL syringe is filled, for example, using a needle inserted into sterile vial, with the clear glucagon solution, and the syringe is placed directly in the pump device after removal of the needle. Alternatively, the needle/syringe may be used to fill a reservoir provided by the pump manufacturer which is then inserted into or as part of the device. At the end of five days, the remaining glucagon solution is discarded and fresh reconstituted glucagon solution is provided to the pump. The dose of glucagon delivered to the subcutaneous tissue will be determined by the needs of the patient. A typical dose used to reverse severe hypoglycemic events is 1 mL of a 1 mg/mL solution.

The present invention will be further understood by reference to the following non-limiting examples.

EXAMPLE 1

Simple Sugars for Glucagon Stabilization

While LMPC is known to improve solubility and stability of glucagon, its use alone with glucagon did not prevent gelation. Prevention of gelation and fibrils is critical since it is possible that cytotoxic amyloidogenic fibrils can form with glucagon (Onoue, S et al., Pharm. Res. 21 p. 1274-1283, 2004), which would make it unsuitable for use in a bihormonal pump or other uses. Therefore, other excipients were tested for their ability to prevent glucagon depredation and gelation. The purpose of this study was to evaluate two sugars, glucose and sucrose, for their effect on stabilizing glucagon.

Materials and Methods

This study compared glucagon stabilization with sucrose and glucose at different concentrations at pH 4.7, 25° C. Glucagon solutions were prepared to a concentration of approximately 1 mg/mL and mixed to a final concentration with either (1) HCl (control), (2) 0.6M glucose, (3) 0.3M glucose, or (4) 0.3M sucrose.

Figure 2:
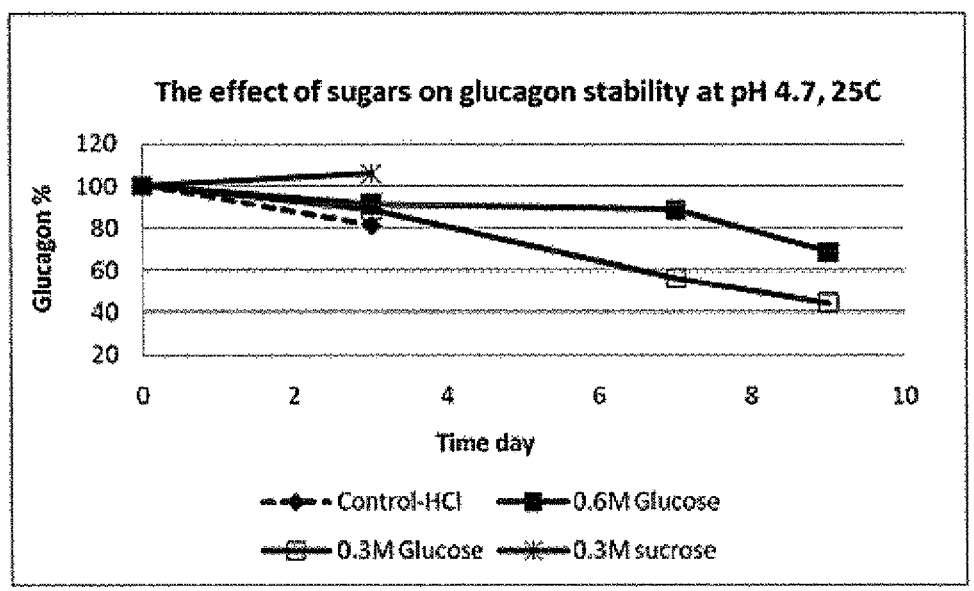
FIG. 2 is a graph of percent remaining glucagon over time (days) at 25° C. at pH 4.7: control HCl (diamond), 0.6M glucose (solid square), 0.3M glucose (empty square), and 0.3M sucrose (-x-).

Results:

Although the sucrose-stabilized glucagon was stable at day 3, it gelled at day 4. The control glucagon in HCl also rapidly degraded and gelled at day 4. 0.6 M glucose was effective to maintain the glucagon at 90% of the original 1 mg/mL dose for 7 days (FIG. 2). A similar result was seen at pH 3.6 and over the temperature range of 25-37° C.

Conclusions:

Glucose alone is effective at preventing gelation. The hypertonic concentrations of glucose (0.6M), though effective at stabilizing glucagon, is likely to create injection site reactions. Therefore, glucose at a physiologic level (0.25-0.3M) is preferable. Since this lower concentration did not provide a sufficient effect on stability, mixing this concentration of glucose with a second stabilizing or solubilizing agent such as LMPC should increase the formulation stability at 37° C.

EXAMPLE 2

Studies Showing the Effect of Different Sugars on the Stability of Glucagon in Combination with LMPC Materials and Methods To further optimize stability during storage, the glucagon was formulated with LMPC in combination with one of several sugars to determine whether the formulation stability could be extended beyond the original glucagon/glucose formulation shown in FIG. 2. The sugars were lactose (90 mg/mL), glucose (45 mg/mL) and glycerin (23 mg/mL). The test sugar+LMPC formulations were compared to LMPC (2 mg/mL) alone following incubation at 37° C. over a period of days.

Results

Figure 3:
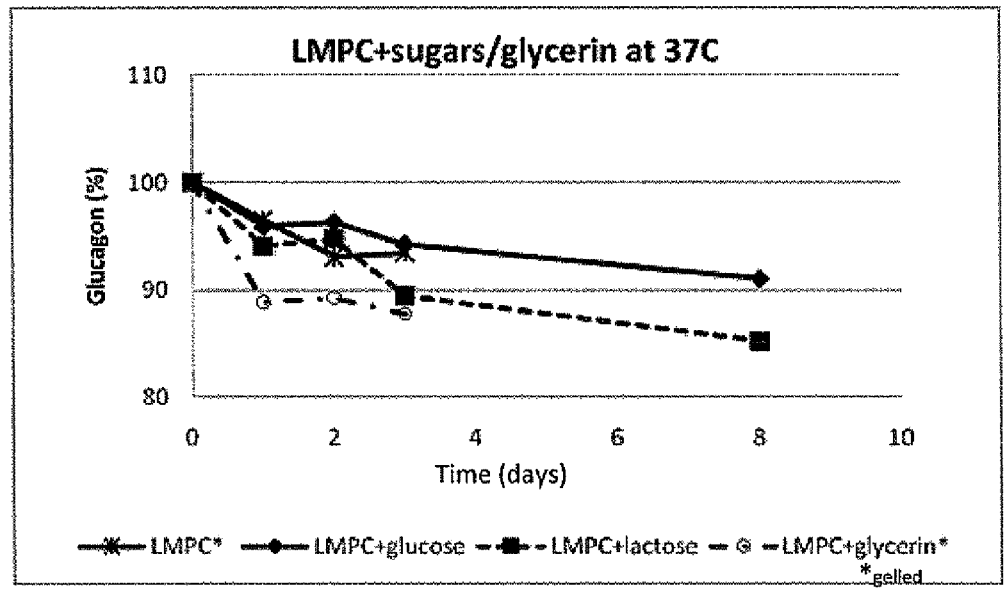
FIG. 3 is a graph of percent glucose in solution over time (days) at 37° C., comparing LMPC alone (star), LMPC+glucose (diamond), LMPC+lactose (square) and LMPC+glycerin (open circle).

The results are shown in FIG. 3. This study found that glucagon with LMPC and glycerin and glucagon and LMPC alone gelled by day six. Lactose and glucose remained in solution to day 8. However, though these were not observed to gel, the glucose was more effective at chemical stabilization of glucagon than lactose. Therefore, glucose in conjunction with LMPC is the preferred combination for glucagon stabilization.

EXAMPLE 3

Development of a Stable Glucagon Formulation for Use in Bihormonal Pumps

The purpose of this study was to add an antibacterial agent to the stabilized glucagon formulation to make it suitable for use with a bihormonal pump (artificial pancreas) at physiological temperatures. Other considerations for pump use include the solution being free of any large particulate matter, gels or fibrils for at least 5 days at 37° C. for the pump to accurately deliver glucagon to the injection site. Also, since the patient is continuously subject to the infusion, the pH of the formulation should be in the pH range of 4-8 to avoid site discomfort. Commercially available formulations of glucagon are not intended for pump use. They are only intended for a single rescue dose of 1 mg and therefore are prepared at a very low pH of approximately 2. These rescue formulations come in a kit containing a lyophilized glucagon powder and a diluent in a separate bottle. These must be combined before use and immediately administered, and according to the label, any excess is to be thrown away because the glucagon is not stable for long periods post reconstitution.

Materials and Methods

A formulation of glucagon referred to as BIOD 901 was designed to be soluble at neutral pH, and have less tendency to gel at 37° C. This was accomplished by combining a simple sugar, glucose; a solubilizing agent, LMPC (lyso-myristoyl-phosphocholine or 1-myristoyl-2-hydroxy-sn-glycero-3-phosphocholine); and a preservative, m-cresol. BIOD 901 contains 1 mg glucagon/mL, 2 mg LMPC/mL, 45 mg glucose/mL, and 2 mg m-cresol/mL, and is made from a basic solution which is adjusted to pH 7.

Figure 4:
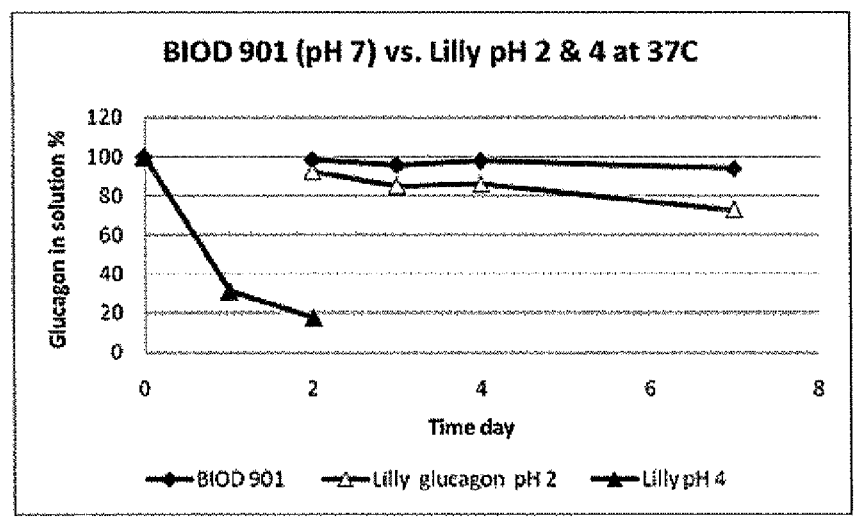
FIG. 4 is a graph of percent glucagon in solution over time (days) at 37° C., in an accelerated stability study of BIOD 901 (diamond) compared to Lilly glucagon at pH 2 (open triangle) and pH 4 (solid triangle).
Figure 5:
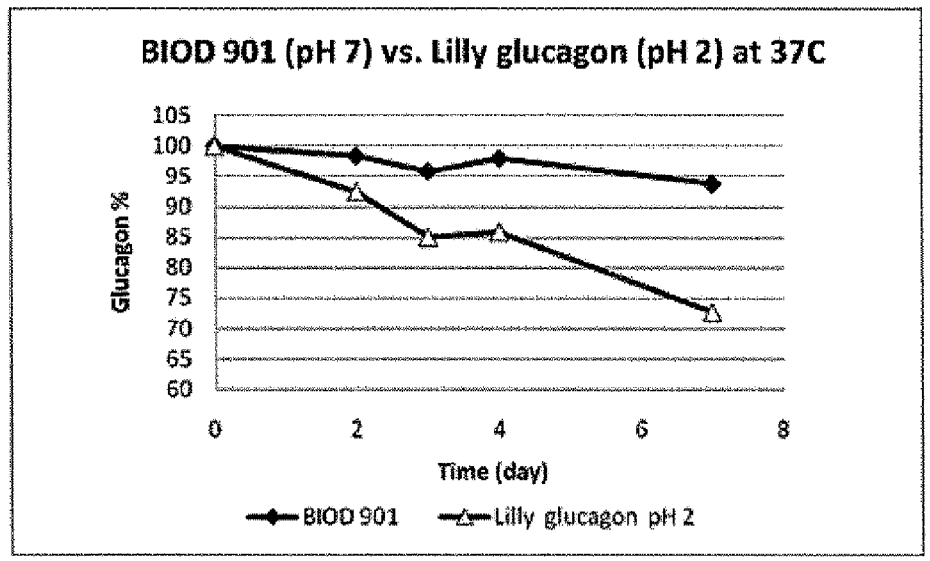
FIG. 5 is a graph of percent glucagon in solution over time (days) at 37° C., comparing BIOD 901 (diamonds) to Lilly glucagon at pH 2 (open triangles).

Results:

General observations of pure glucagon powder in solution at pH 4 show that it gels within 2 days. Glucagon from a commercially available rescue kit at pH 2 does not gel, but instead chemically degrades over time and drops to less than 90% potency in three days at 37° C. Adjustment of this formulation to pH 4 hastened the decomposition by precipitation (FIG. 4). FIG. 5 shows the improvement in chemical stability of BIOD 901 over the Lilly glucagon formulation at pH 2. The pH adjustment to 4 was tested in an effort to reduce the acidity of the formulation, making it more suitable for pumping into the near neutral pH subcutaneous tissue.

The Lilly glucagon prepared at pH 2 lost 15% to chemical degradation by day 3, while less than 10% of BIOD 901 was degraded by day 7. Elevation of the Lilly glucagon pH to 4 resulted in precipitation of the glucagon on the first day, as shown by the rapid loss in active concentration in FIG. 4. In addition to chemical degradation, gelation is also of concern, particularly during pump use. BIOD 901 began to gel after ten days, well beyond the required seven days. The glucagon formulation made with a combination of LMPC, glucose and preservative was more stable compared to glucagon with LMPC, as shown in FIG. 3.

Conclusion:

In summary, BIOD 901 is more chemically and physically stable at 37° C. than commercial Lilly glucagon and has the added benefit of a physiological pH, which is more suitable for pumping into subcutaneous tissue than an acidic pH of 2.

EXAMPLE 4

Comparison of Alternative Preservatives: M-Cresol and Sodium Benzoate

Due to incompatibilities with some plastic storage containers, an alternative to m-cresol was tested with BIOD 901. The two test formulation consisted of 2 mg/mL LMPC, 45 mg/ml glucose and 1 mg/ml glucagon, and either m-cresol or sodium benzoate, 0.5 mg/mL.

Methods:

Glucagon powder was first dissolved into the lipid solution at a concentration of 2 mg/mL glucagon and 4 mg/mL of lipid. Concentrated glucose, m-cresol/sodium benzoate solution was then added to the solution and briefly mixed. The final concentrations were 1 mg/mL glucagon, 2 mg/mL LMPC, 45 mg/mL glucose and 2 mg/mL preservative (m-cresol or sodium benzoate). The solution pH was adjusted to about 7 and samples were filtered through a 0.2 µm filter and placed in a 37° C. chamber. Samples were analyzed by HPLC.

Figure 6:
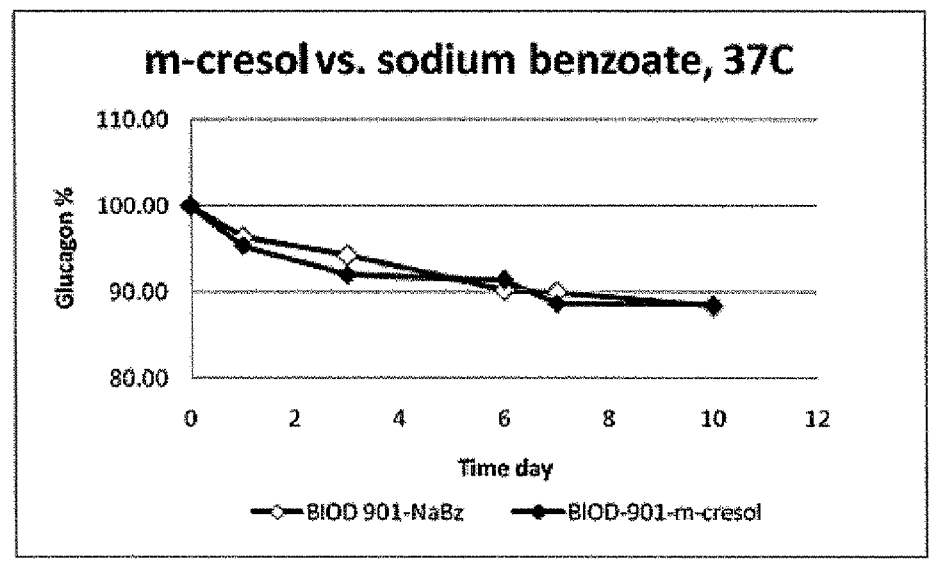
FIG. 6 is a graph of percent glucagon over time (days) at 37° C., comparing two preservatives, sodium benzoate (open diamonds) and m-cresol (closed diamonds), in glucagon formulation BIOD 901.

Results:

The remaining glucagon (as a function of time) of the two formulations is graphed in FIG. 6. The results in FIG. 6 show the average percent glucagon remaining in solution was essentially the same with either sodium benzoate or m-cresol. Therefore either can be effectively used with the formulation.

EXAMPLE 5

In Vivo Glucose Response to Glucagon Administration in Diabetic Miniature Swine

This study was designed to assess the effectiveness of glucagon formulations exposed to 37° C. for 3 days to increase blood glucose after subcutaneous administration to diabetic miniature swine. BIOD 901 and Lilly glucagon were compared, either freshly prepared or following incubation for 3 days at 37° C. The study consisted of a crossover design using 5 diabetic miniature swine.

Materials and Methods:

Five diabetic miniature swine were fed a full breakfast at 7:30 am on the morning of the study and given a prandial insulin with their food. Three hours later, additional insulin was given intravenously, and glucose was tested every 10 minutes to determine when the glucose had dropped to a level of 50 µL mg/dL. When this glucose level was established, a dose of 50 µL of test glucagon formulation (1 mg/mL) was given by subcutaneous injection. Glucose levels were monitored every 10 minutes for 90 minutes post dose to demonstrate the effectiveness of the glucagon to elevate glucose levels in the swine.

Figure 7A:
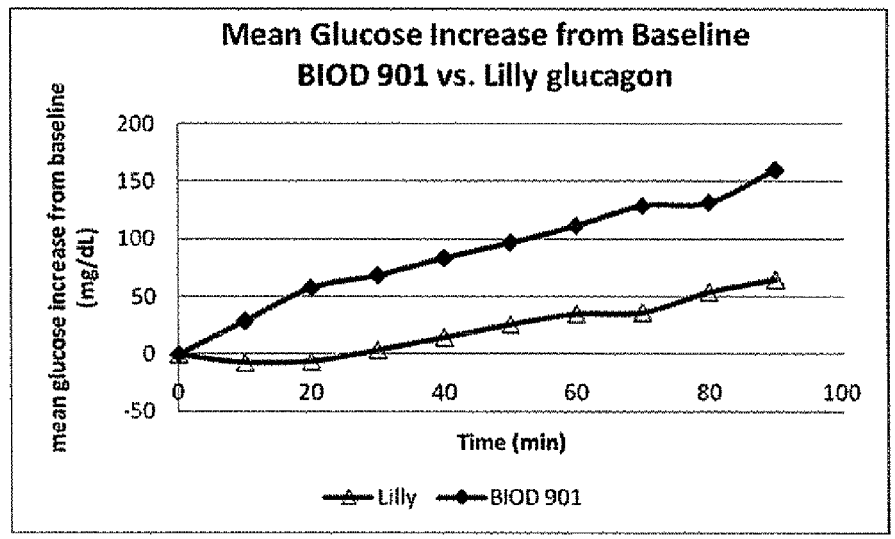
FIG. 7a is a graph of the baseline corrected increase in glucose values (mg/dl) over time following glucagon administration to miniature diabetic swine, comparing Lilly glucagon pH 2 (open triangles) versus BIOD 901, (solid diamonds).
Figure 7B:
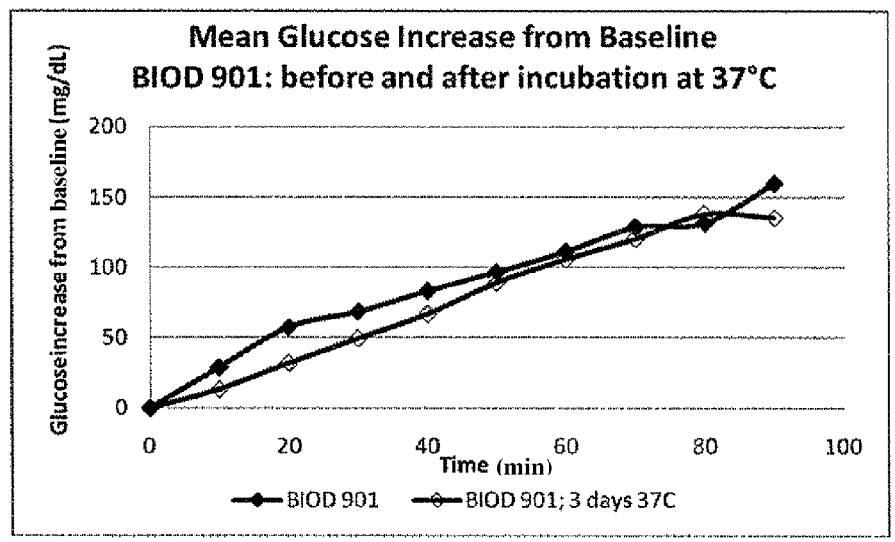
FIG. 7b is a graph of the baseline corrected increase in glucose values over time (days) following glucagon administration to miniature diabetic swine, comparing BIOD 901 freshly prepared (solid diamonds) to a sample that was incubated 3 days at 37° C. (open diamonds) for the BIOD 901.

Results:

FIG. 7a shows the mean increase from baseline of blood glucose over time (post glucagon administration) to the same five swine given either BIOD 901 stored 24 hours at 4° C. or Lilly glucagon freshly prepared on the morning of the study. The pigs responded well to the glucagon, elevating their glucose levels considerably post injection. FIG. 7b is a graph of the mean increase from baseline of blood glucose over time of BIOD 901 before and after 3 days at 37° C. The almost superimposable results show that there was no apparent change in efficacy of the glucagon after incubation at 37° C.

Conclusion:

This data confirms that the BIOD 901 formulation at pH 7 is very effective at increasing blood glucose in diabetic miniature swine, even after being stressed for 3 days at 37° C.

EXAMPLE 6

Demonstration of Detection of Gelation by Light Obscuration Technique and Malvern Size Distribution Physical changes in the glucagon solution, such as gelling or precipitation, can be quantitated by observing the obscuration of light through a sample of the formulation. A simple device comprised of a light source and detector was set up in an enclosed box and data recorded by specially designed computer software for this application.

Materials and Methods:

BIOD 901 was inserted into the chamber, and observed over 60 days at room temperature (approximately 25° C.). The light intensity was recorded over time (work days).

Figure 8:
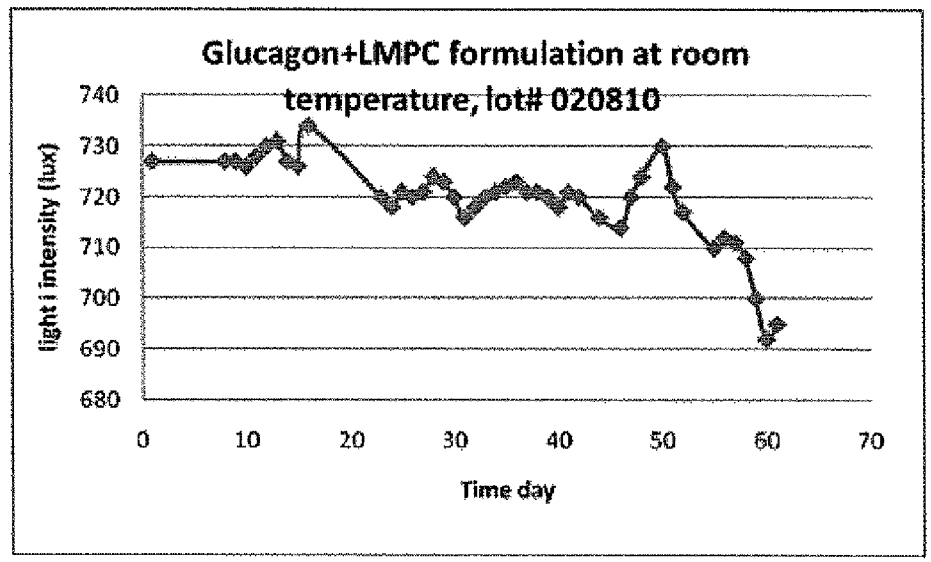
FIG. 8 is a graph of the light intensity over time in days, showing the decline in light intensity (obscuration) after gel formation in formulation BIOD 901 at around 60 days at 25° C.

Results:

The light intensity over time is graphed in FIG. 8. Between day 50 and 60, there was a considerable drop in intensity that coincided with the appearance of gelation. The fresh formulation was also tested for Malvern size distribution and compared to the formulation after 60 days in a cuvette. Initially, the primary Malvern particle size was about 6.5 nm. After 60 days it increased to about 10 nm.

Conclusion:

Gelation can be detected and quantitated by either a decrease in light transmittance through the formulation over time, or by an increase in the primary glucagon particle size distribution.

EXAMPLE 7

Effect of Ethanol Concentration on Reduction of Gelation

In an effort to reduce gelation, particularly at 4° C., 1-10% ethanol was added to BIOD 902 and compared to the formulation without ethanol at 4, 25 and 37° C.

Results:

The following table shows the chemical degradation (% glucagon) of glucagon at 25° C. following addition of various amounts of ethanol to BIOD 902. Upon gelation, the sample was no longer assayable by HPLC.

TABLE 1

Effect of Ethanol Concentration on Glucagon Stability: percent glucagon remaining after incubation at 25° C.

| Time (day) | 0% | 2% | 5% | 10% | 20% | 40% |
|---|---|---|---|---|---|---|
| 0 | 100 | 100 | 100 | 100 | 100 | 100 |
| 1 | 96 | 101 | 103 | 103 | 101 | 100 |
| 2 | 96 | 96 | 97 | 96 | 95 | 94 |
| 3 | 93 | 98 | 97 | 101 | 98 | 93 |
| 6 | 97 | 101 | 97 | 106 | gelled | 99 |
| 10 | 93 | 92 | 96 | gelled | | gelled |
| 18 | 94 | 93 | 93 | | | |
| 26 | 86 | 90 | 90 | | | |
| 32 | gelled | 86 | gelled | | | |

This study shows that addition of 2% ethanol to the BIOD 902 formulation can be useful in protecting glucagon against gelation, further extending its shelf life.

EXAMPLE 8

Addition of Benzyl Alcohol as an Alternative Antimicrobial in BIOD 902

Materials and Methods:

This study was a short term stability test to examine the effect on stability of benzyl alcohol as an antimicrobial agent in BIOD 902 compared to sodium benzoate. Two mg/mL of sodium benzoate or benzyl alcohol were added to each formulation (instead of m-cresol).

Figure 9:
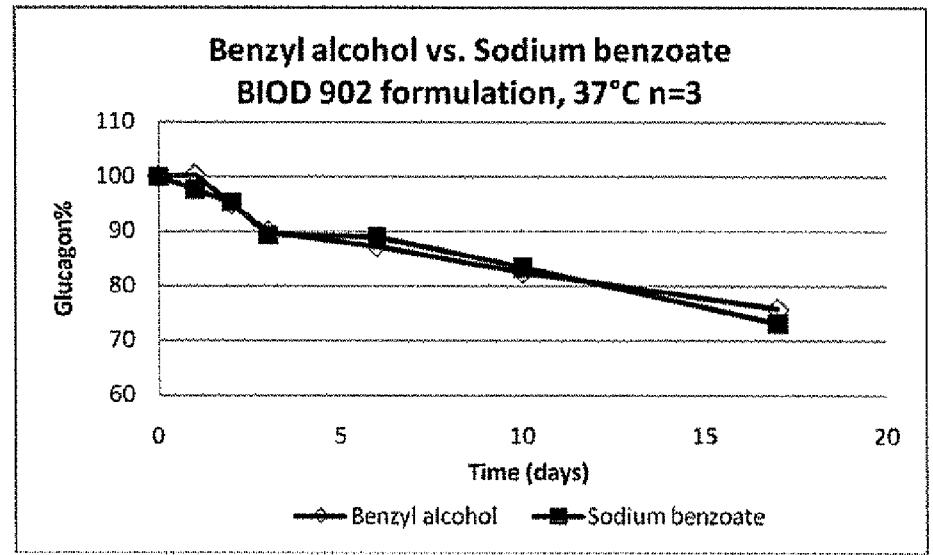
FIG. 9 is a graph of percent glucagon over time for two variations of BIOD 902, using 2 mg/mL of either benzyl alcohol (open diamond) or sodium benzoate (solid square) as an antimicrobial agent instead of m-cresol.

Results:

Results shown in Example 4 demonstrated that m-cresol and sodium benzoate did not alter the degradation profile of glucagon in BIOD 901. Comparison of sodium benzoate to benzyl alcohol in BIOD 902 showed similar results (FIG. 9).

Conclusion:

In conclusion, m-cresol, sodium benzoate or benzyl alcohol may be used as an antimicrobial in formulations BIOD 901 or 902.

Modifications and variations of the present invention will be obvious to those skilled in the art from the foregoing detailed description and are intended to come within the scope of the following claims. The teachings of all references cited herein are specifically incorporated by reference.

We claim:

1. A stabilized glucagon formulation comprising Glucagon,
   a surfactant, and
   a monosaccharide,
   wherein the surfactant and monosaccharide are in an effective amount to enhance the stability of glucagon, as compared to the stability of glucagon in combination with the surfactant, and
   wherein the osmolarity is approximately 200 to 400 mOsm and the pH is between 2 and 8.

2. The formulation of claim 1 wherein the pH of the solution is between 5 and 7.6 and the osmolarity is between 240 and 310 mOsm.

3. The formulation of claim 1 wherein the surfactant is a lysophospholipid, phospholipid, glycerophospholipid or amphiphilic block copolymer.

4. The formulation of claim 3 wherein the surfactant is myristoyl lysophosphocholine.

5. The formulation of claim 1 wherein the monosaccharide is a monosaccharide with an alkyl chain length ranged from C8 to C12.

6. The formulation of claim 5 wherein the monosaccharide is glucose.

7. The formulation of claim 1 further comprising a preservative.

8. The formulation of claim 1 wherein the concentration range for the glucagon is between 0.5 and 5 mg/mL; monosaccharide is between 20 and 100 mg/mL; and surfactant is between 0.1 and 10 mg/mL.

9. The formulation of claim 8 wherein the concentration range for the glucagon is between 0.8 and 1.5 mg/mL; monosaccharide is between 36 and 72 mg/mL, and surfactant is between 0.5 and 5 mg/mL.

10. The formulation of claim 1 comprising a preservative in a concentration of between 0.2 and 3 mg/mL.

11. The formulation of claim 1 comprising up to 10% ethanol.

12. The formulation of claim 11 comprising about 2% ethanol.

13. The formulation of claim 1 wherein the pH of the formulation is in the physiological range.

14. The formulation of claim 1 wherein the pH of the formulation is in the acidic range.

15. The formulation of claim 1 comprising a microemulsion.

16. The formulation of claim 1 comprising micelles.

17. The formulation of claim 1 comprising a microprecipitate.

18. The formulation of claim 1 comprising a reconstitutable powder.

19. The formulation of claim 15 wherein the glucagon is provided in a two vial kit with one vial containing glucagon and a second vial containing diluent, wherein the glucagon is reconstituted with diluent immediately before use.

20. The formulation of claim 1 wherein the glucagon is administered in a pump.

21. The formulation of claim 1 wherein the glucagon is provided in a single vial as a solution in either the liquid or frozen state.

22. A method of making a stable glucagon solution comprising providing the formulation of claim 1.

23. A method of treating diabetes or hypoglycemia in a patient in need thereof comprising administering the glucagon formulation of claim 1.

* * * * *